United States Patent [19]

Rassman

[11] Patent Number: 5,584,841
[45] Date of Patent: Dec. 17, 1996

[54] INSTRUMENT FOR IMPLANTING HAIR GRAFTS

[76] Inventor: William R. Rassman, 29391 Laro Dr., Agoura, Calif. 91310

[21] Appl. No.: 444,923

[22] Filed: May 19, 1995

[51] Int. Cl.$^6$ ................................................. A61B 17/00
[52] U.S. Cl. ........................................ 606/132; 606/187
[58] Field of Search ..................... 606/185, 186, 606/187, 131, 132, 133, 11, 7; 227/134, 176, 177; 623/15; 604/57, 59, 61, 62

[56] References Cited

U.S. PATENT DOCUMENTS

| | | | |
|---|---|---|---|
| 4,126,124 | 11/1978 | Miller | 606/187 |
| 4,451,254 | 5/1984 | Dinius et al. | |
| 5,417,683 | 5/1995 | Shiao | 606/1 |
| 5,439,475 | 8/1995 | Bennett | 606/187 |

FOREIGN PATENT DOCUMENTS

94/07433  4/1994  WIPO.

OTHER PUBLICATIONS

Brandy et al., "Utilization of No-kor Needles for Slit-Micrografting," Elsevier Science Inc., Jun. 1994.
James Arnold, "Pursuing the Perfect Strip: Harvesting Donor Strips with Minimal Hair Transection", International Journal of Aesthetic and Restorative Surgery, vol. 3, No. 2, 1995, pp. 148–153.
Robert M. Bernstein, et al., "Follicular Transplantation", International Journal of Aesthetic and Restorative Surgery, vol. 3, No. 2, 1995, pp. 119–132.
William R. Rassman, et al., "The Art and Science of Micrografting", Reprint from International Journal of Aesthetic and Restorative Surgery, vol. 1, No. 1, 1993, pp. 27–36.
William R. Rassman, et al., "Micrografting in Extensive Quantities", Reprint from Dermatologic Surgery, vol. 21, No. 4, Apr. 19, 1995, pp. 306–311.

William R. Rassman, "Megasessions: Dense Packing", Hair Transplant Forum International, vol. 4, No. 3, May–Jun. 1994.
Richard C. Shiell, "An Australian View of the Las Vegas Meeting", Hair Transplant Forum International, vol. 5, No. 5, Sep.–Oct. 1995.
Michael Beehner, "1995 Las Vegas ISHRS Meeting", Hair Transplant Forum International, vol. 5, No. 5, Sep.–Oct. 1995.
William R. Rassman, "One of our greatest problems . . . Lowballing!", Hair Transplant Forum International, vol. 2, No. 6, Jul.–Aug. 1992.
William R. Rassman, "Concern About Quality", Hair Transplant Forum International, vol. 4, No. 4, Jul.–Aug. 1994.
Michael D. Sparkuhl, "Hair Transplant Surgery The Next Generation", Hair Transplant Forum International, vol. 4, No. 4, Jul.–Aug. 1994.
William R. Rassman, "Trouble With Megasessions and Dense Packing", Hair Transplant Forum, vol. 5, No. 6, Nov.–Dec. 1995.
New Hair Newsletter, vol. 1, No. 3, New Hair Institute, Fall/Winter 1995.

(List continued on next page.)

*Primary Examiner*—Robert A. Hafer
*Assistant Examiner*—Benjamin Koo
*Attorney, Agent, or Firm*—Fitzpatrick, Cella, Harper & Scinto

[57] ABSTRACT

A method of and instrument for use in micrograft implantation of hair grafts which typically include only one or at most a few hair follicles. A scalp incision is made with the tip of a microsurgical blade. A follicle end of a hair graft is grabbed with a grabbing edge and dragged down a surface of the microsurgical blade to the base of the incision, all the while leaving the tip of the microsurgical blade in place in the scalp incision. The microsurgical blade is withdrawn from the scalp incision while holding the hair graft in place at the base of the scalp incision with the grabbing edge. Finally, the grabbing edge is withdrawn from the scalp incision while leaving the hair graft implanted in the scalp incision.

15 Claims, 4 Drawing Sheets

OTHER PUBLICATIONS

Robert M. Bernstein, "Hair Restoration: Answered Questions.", Reprint from Dermatologic Surgery, vol. 22, 1996, pp. 97–98.

O'Tar T. Norwood, "Gearing Up for Two Thousand Grafts Per Session and Dense Packing", Hair Transplant Forum International, vol. 4, No. 4, Jul.–Aug. 1994.

William R. Rassman, "The Minigraft Revolution: Can We Keep Up Ethically?", Reprint from The American Journal of Cosmetic Surgery, vol. 11, No. 2, 1994, pp. 103–104.

New Hair Institute Update, from Spring 1995 Newsletter, New Hair Institute.

The Fast Track Option: A Common Sense Approach To Hair Transplantation, William R. Rassman, New Hair Institute, ©1994, 1995.

Hair Today And Tomorrow: An Overview of Old Wives Tales, Wigs, Lotions, Potions, Fact, Fiction and Medical Hair Restoration Options, Marc A. Pomerantz, et al., ©Aug., 1993.

A Buyer's Guide To Hair Transplantation: The Answers Are In The Details, William R. Rassman, New Hair Institute, ©1993.

Videotape entitled "New Hair: The Truth About Transplants", New Hair Institute, ©1994.

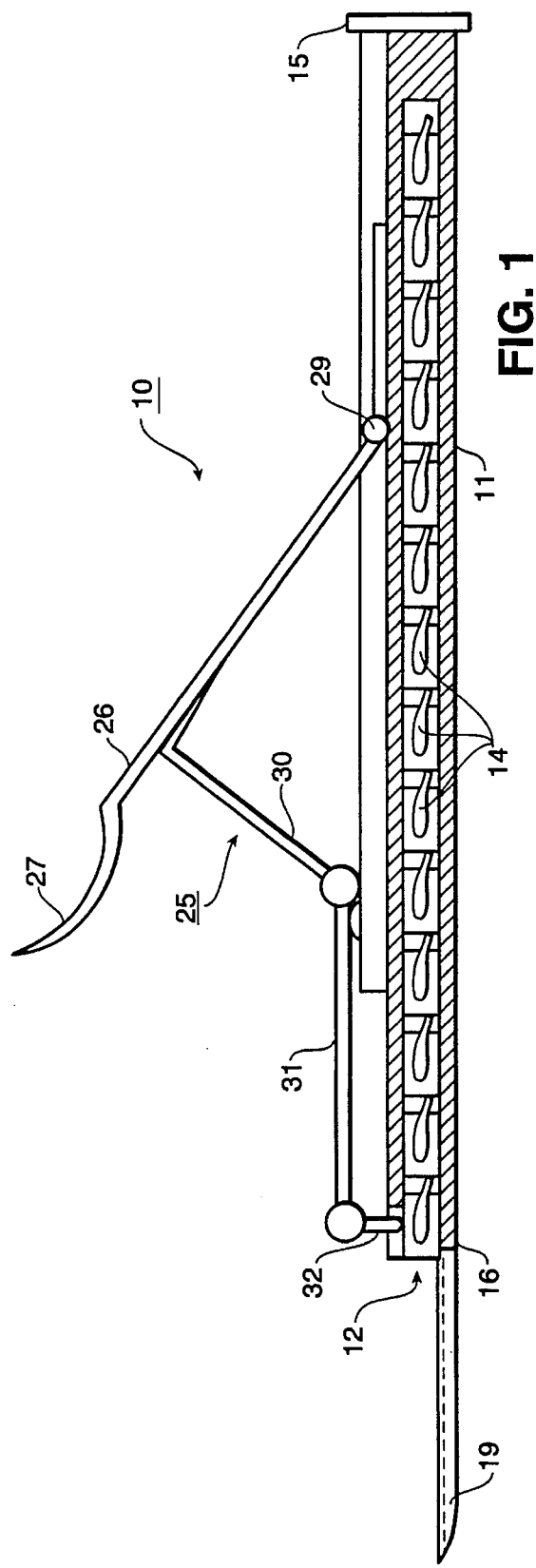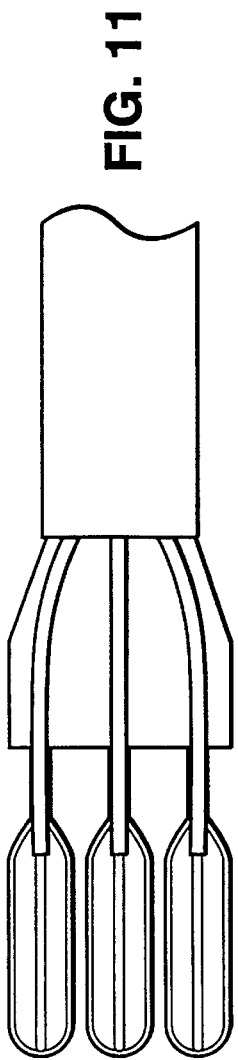

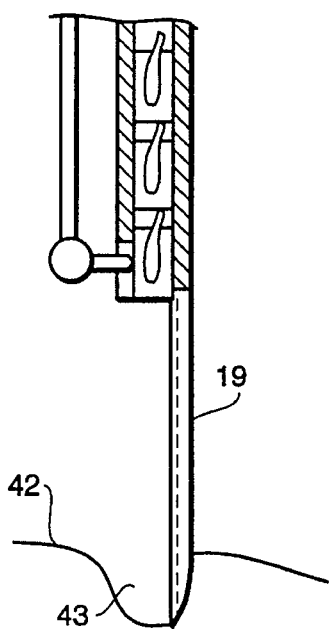
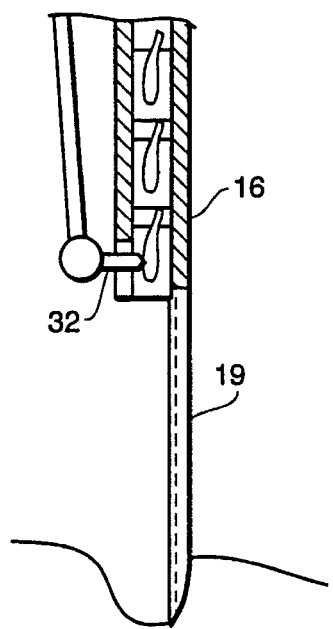
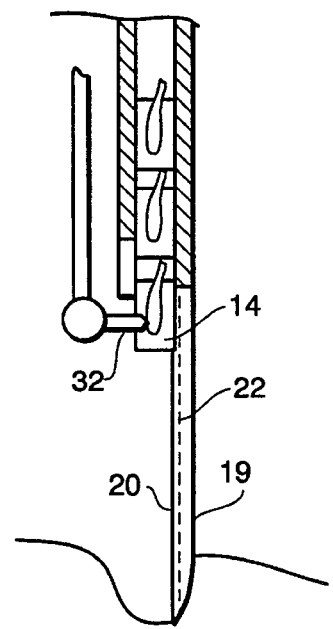
FIG. 5　　　FIG. 6　　　FIG. 7
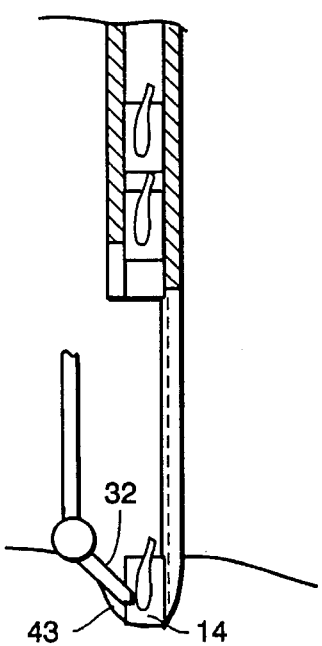
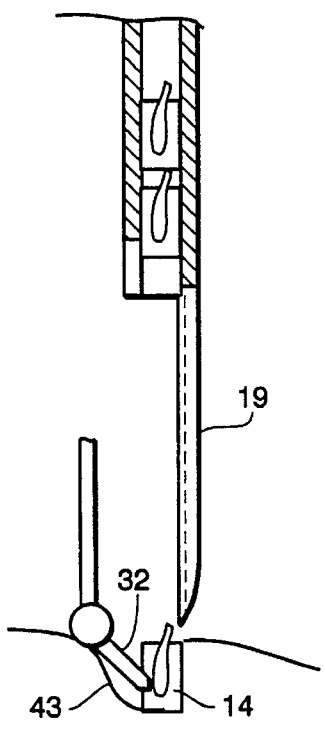
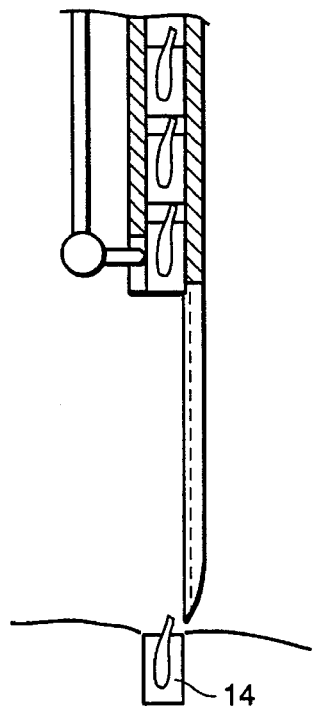
FIG. 8　　　FIG. 9　　　FIG. 10

INSTRUMENT FOR IMPLANTING HAIR GRAFTS

BACKGROUND OF THE INVENTION

1. Field of the Invention

The present invention relates to a method and apparatus for making a scalp incision and implanting a hair graft therein.

2. Description of the Related Art

Hair transplantation techniques from years past have involved harvesting hair from the back or side of the scalp where it grows permanently, creating hair grafts which typically included 25 to 35 hair follicles in each, and implanting the hair grafts in the front, top and crown of the head where genetic balding produces hair loss. While advantageous in providing hair where none previously existed, such techniques produced visually unsightly results, commonly referred to as a "corn field" in that each hair graft is widely separated from other hair grafts and each hair graft has concentrated plugs of 10 to 35 hair follicles each.

In recent years, the inventor of the present invention has pioneered a technique known as the fast-track in which many hair micrografts (each containing 1 to 4 hair follicles) are implanted in a single surgery. When implanted in closely spaced relationship to each other, such micrografts produce a very natural looking appearance closely simulating a natural hair distribution.

As a result of the large number of grafts which are placed in a single session, the laborious method heretofore previously used, has caused the surgery time to extend from 1 to 2 hours, to 8 to 13 hours. Specifically, because the grafts consist of one or at most a few hair follicles, each graft is quite small and difficult to implant in the scalp. For example, in an effort to insert a micrograft into a scalp incision, it has been considered simply to grasp the body of the micrograft with forceps and push or pull the micrograft into the scalp incision. Such a technique has the potential to damage the hair follicle. Specifically, because of the small size of both the incision and the graft, using forceps to push or pull the graft into the incision only deforms the graft, with the graft sometimes being damaged when additional pushing or pulling pressure is applied in an attempt to force the graft into position.

Moreover, it is necessary to implant many hundreds to several thousands of grafts to produce a natural-looking hair distribution.

Because of the difficulty of each graft and the number of such grafts needed, a typical micrografting session on a single patient can last for 8 to 13 hours and involve more than a dozen technicians as well as the surgeon.

Accordingly, there exists a need for an implantation instrument which both eases the process and speeds the fast-track procedure.

SUMMARY OF THE INVENTION

The present invention addresses the above-noted need by providing a technique by which a graft is dragged, from the base thereof, into place at the bottom of a scalp incision. Because the graft is dragged rather than pushed, the graft is generally not deformed and is rarely ever damaged. Moreover, because the invention uses a one-way grabbing device to grab the base end of a hair graft and drag the hair graft into position in a scalp incision, it is a simple matter to retract the grabbing device from the scalp incision and leave the hair graft in place, since the grabbing device slides along the graft as it is being removed from the scalp.

The invention also provides an instrument, as well as a method usable with the instrument, for making a scalp incision and implanting hair grafts therein.

According to one aspect of the invention, an instrument which makes a scalp incision and implants a hair graft therein includes an elongate housing adapted to be manipulated by a surgeon during implantation of hair grafts, the elongate housing having a through bore for holding a supply of hair grafts and for feeding the hair grafts in a follicle-down orientation to a feed position. A microsurgical blade adapted to make the scalp incision is arranged at the feed position of the elongate housing. The microsurgical blade has a longitudinally planar surface terminating in an incision tip, the longitudinally planar surface being adapted to guide a hair graft from the feed position to the incision tip. A trigger actuated feed mechanism is fixed to the housing and is adapted for trigger actuation by the surgeon between an unactuated position and a fully actuated position. The feed mechanism includes a puller assembly terminating in a grabbing edge which, in the unactuated position, is positioned at the feed position adjacent the planar surface of the microsurgical blade, and which, in the fully actuated position, extends beyond the incision tip of the microsurgical blade. The grabbing edge is configured so that during manipulation from the unactuated position to the fully actuated position, it grabs the follicle end of a hair graft at the feed position, slides the hair graft along the planar surface of the microsurgical blade, delivers the hair graft to the incision tip, and extends beyond the incision tip while the incision tip is withdrawn from the scalp incision, thereby to hold the hair graft in place at the base of the scalp incision.

In another aspect, the invention is a method for micrograft implantation of hair grafts in a scalp incision. The method includes making a scalp incision with a microsurgical blade, grabbing a follicle end of a hair graft with a pulling mechanism, and sliding the hair graft down a surface of the microsurgical blade to the base of the scalp incision using the pulling mechanism while leaving the tip of the microsurgical blade in place in the scalp incision. The microsurgical blade is withdrawn from the scalp incision while holding the hair graft in place at the base of the scalp incision with the pulling mechanism. The pulling mechanism is thereafter withdrawn from the scalp excision leaving the hair graft implanted in the scalp incision.

This brief summary has been provided so that the nature of the invention may be understood quickly. A more complete understanding of the invention can be obtained by reference to the following detailed description of the preferred embodiment thereof in connection with the attached drawings.

BRIEF DESCRIPTION OF THE DRAWINGS

FIG. 1 is a cross-sectional view of an instrument for implanting hair grafts.

FIG. 2 is a cross-sectional view emphasizing a feed mechanism for feeding hair grafts.

FIGS. 5 to 10 are schematic views showing, in sequence, operation of the FIG. 1 instrument.

FIG. 11 is a plan view showing an alternate embodiment.

DETAILED DESCRIPTION OF THE PREFERRED EMBODIMENTS

Figure 3A:
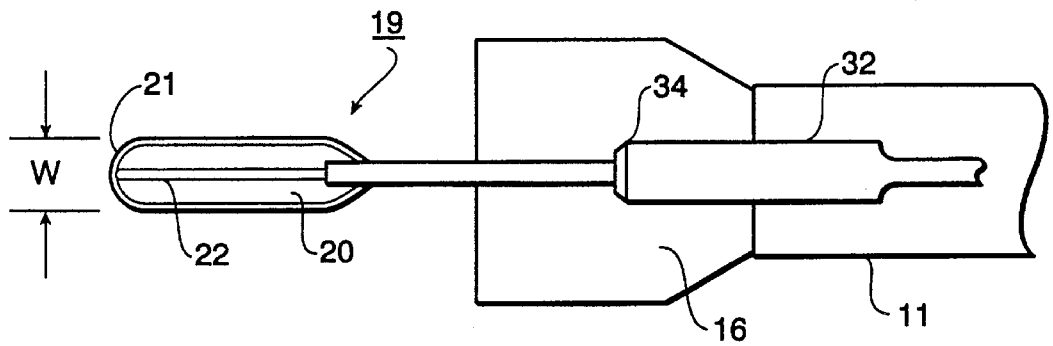
FIGS. 3(a) to 3(c) are plan views showing three different arrangements for a grabbing edge.

FIG. 1 is a cross-sectional view of an instrument 10 designed to make a scalp incision and implant a micro-hair graft in the scalp of a patient.

As shown in FIG. 1, instrument 10 includes a housing 11 which preferably is elongate so as to permit manipulation by a surgeon in much the same way as a pen or pencil. Housing 11 includes a through bore 12 which is dimensioned so as to hold a supply of hair grafts 14. Each hair graft is positioned in a follicle-down orientation in through bore 12, and preferably each hair graft includes one or no more than a few (three to five) hair follicles each.

If desired, the supply of hair grafts 14 may be carried in a removable tube (not shown) which is inserted into elongate housing 11 via cap 15. In any event, the supply of hair grafts 14 is biased towards a feed position 16 of housing 11 by biasing means which may include simple gravity feed as in the case shown in FIG. 1. Alternatively, it is possible as shown in FIG. 2 to include biasing means in the form of a spring 17 or to include other biasing means such as a source of air pressure. In any event, through use of biasing means, the supply of hair grafts 14 is biased in through bore 12 towards feed position 16, as noted above.

Returning to FIG. 1, a microsurgical blade 19 is arranged at the feed position 16 of elongate housing 11. Microsurgical blade 19 is shown in plan views in FIGS. 3(a) through 3(c). Referring, for example, to FIG. 3(a), microsurgical blade 19 includes a longitudinally planar surface 20 terminating in an incision tip 21. The longitudinally planar surface 20 is adapted to guide a hair graft from feed position 16 to incision tip 21. Preferably, longitudinally planar surface 20 includes a groove 22 which assists in guiding the hair graft from the feed position to the incision tip. Preferably, the width W of incision blade 19 is between 0.25 and 0.50 mm.

Referring again to FIG. 1, a trigger actuated feed mechanism 25 includes a lever 26 terminating in a trigger-shaped loop 27 and pivoted at 29 to housing 11. Lever 26 actuates push rod assembly 30, 31 which terminates in a grabbing edge 32. The trigger-actuated feed mechanism 25 is adapted for trigger-actuated manipulation by the surgeon between an unactuated position and a fully actuated position, as described more fully below.

Figure 3B:
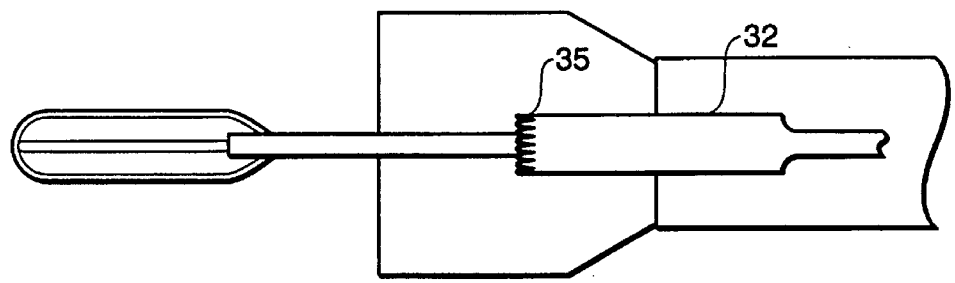
Figure 3C:
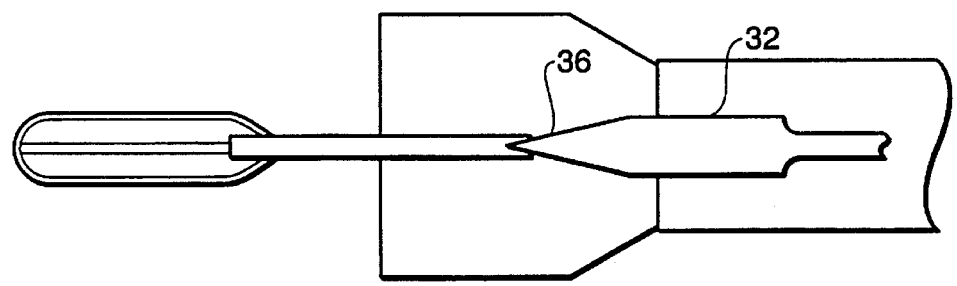

Grabbing edge 32 is configured to grab the base (or follicle) end of a hair graft 14 at feed position 16, to slide the hair graft along the planar surface 20 of microsurgical blade 21, to deliver hair graft 14 to incision tip 21, and thereafter to extend beyond the incision tip while the incision tip is withdrawn from a scalp incision. Accordingly, grabbing edge 32 is configured as a one-way grabbing device, meaning that it is able to grab a hair graft at a base thereof while moving in one direction, yet is able to slide easily over the hair graft while moving in the other direction. FIGS. 3(a) through 3(c) illustrate three different possible embodiments of grabbing edge 32, all of which exhibit the desired one-way grabbing characteristics.

Referring first to FIG. 3(a), grabbing edge 32 includes a chisel-shaped tip 34 which is designed to grab the follicle end of a hair graft and slide it along planar surface 20 of incision blade 19. Because grabbing edge 32 includes a chisel-shaped tip 34, the edge is easily able to retract over the graft while leaving the graft in place at the base of a scalp incision.

In FIG. 3(b), grabbing edge 32 includes serrated edge 35 which is also able to grab the follicle end of a hair graft and slide it along the planar surface 20 of incision blade 19, yet at the same time is able to retract easily over the hair graft while leaving it in place at the base of a scalp incision.

Finally, referring to FIG. 3(c), grabbing edge 32 includes a pointed tip 36 which is also able to provide one-way grabbing of the follicle end of hair graft 14 yet, at the same time, is able to retract easily over the hair graft leaving the hair graft in place at the base of a scalp incision.

In FIGS. 3(a) and 3(b), grabbing edge 32 has a width wider than that of groove 22. This arrangement is preferred since it allows the grabbing edge to extend beyond the groove and ride on shoulders of the groove, thereby cushioning hair grafts between the grabbing edge within the confines of groove 22. Such an arrangement tends to cause less damage to the hair graft.

Figure 4:
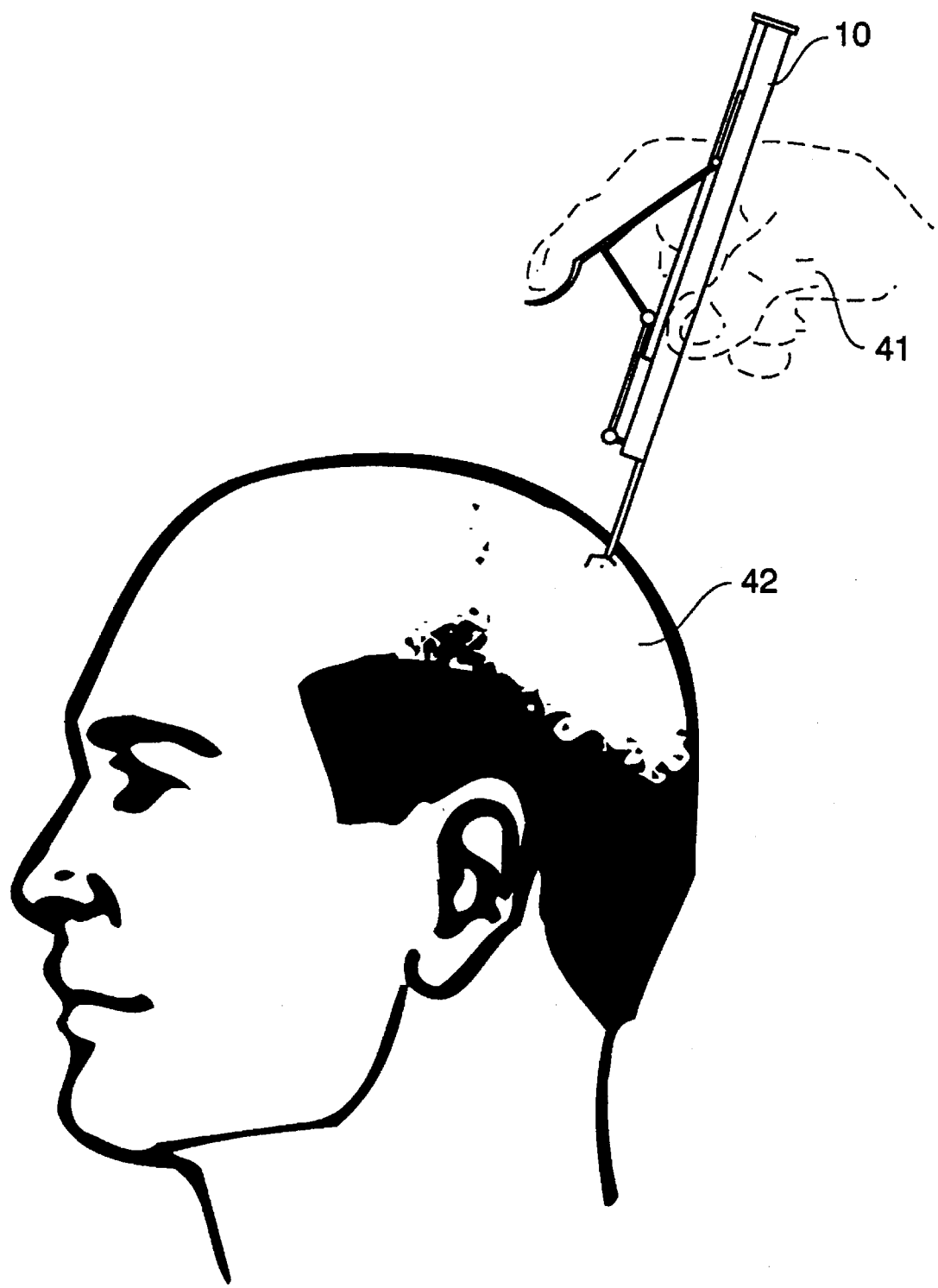
FIG. 4 is a schematic view of a hair implantation procedure.

FIG. 4 shows use of implantation instrument 10 as it is manipulated by a surgeon's hand 41 so as to make scalp incisions in the scalp 42 of a patient and implant hair grafts in each scalp incision. Generally speaking, the surgeon manipulates instrument 10 so as to make a scalp incision with microsurgical blade 19, grab a follicle end of a hair graft at feed position 16 with grabbing edge 32, actuate the trigger assembly 25 so as to drag a hair graft down planar surface 20 of microsurgical blade 19 into the scalp incision toward the bottom thereof, while leaving the tip 21 of the microsurgical blade in place in the scalp incision, withdraw the microsurgical blade from the scalp incision while holding the hair graft in place at the base of the scalp incision with grabbing edge 32, and then withdraw the grabbing edge 32 while leaving the hair graft implanted in the scalp incision. FIGS. 5 through 10 illustrate this process in more detail.

Thus, as shown in FIG. 5, a surgeon has manipulated incision blade 19 so as to create a scalp incision 43 in scalp 42. In FIG. 6, the surgeon has actuated the trigger mechanism so as to grab the follicle end of the hair graft 14 that is positioned at feed position 16. FIG. 7 shows continued actuation of trigger mechanism 25 so as to drag hair graft 14 down planar surface 20 of incision blade 19. Preferably, incision blade 19 will be provided with groove 22 which assists in dragging hair graft 14 down planar surface 20, into incision 43, and towards the bottom of the incision at the tip of the incision blade.

FIG. 8 shows hair graft 14 guided completely down the surface of the incision blade to the base of scalp incision 43. Then, as shown in FIG. 9, the surgeon withdraws the incision blade from scalp incision 43 while continuing to actuate trigger mechanism 25. As noted above, continued actuation of trigger mechanism 25 causes grabbing edge 32 to extend beyond the tip of incision blade 19. This arrangement permits hair graft 14 to be held in place by grabbing edge 32 while incision blade 19 is withdrawn from the scalp incision 43, without disturbing the positioning of the hair graft at the base of the scalp incision. Finally, as shown in FIG. 10, grabbing edge 32 is also withdrawn from the scalp incision, by sliding the grabbing edge over the surface of the graft. As explained above, due to the one-way characteristics of grabbing edge 32, hair graft 14 is left implanted in the scalp incision as the edge is retracted. As the surgeon releases pressure on trigger mechanism 25, the trigger mechanism returns to its unactuated state, which, in turn, returns grabbing edge 32 to feed position 16 in preparation for feeding the next hair graft 14.

Those skilled in the art will recognize that various modifications of the foregoing embodiments can be made without departing from the scope and spirit of the invention as defined in the appended claims. For example, as shown in FIG. 11, it is possible to provide for plural incision blades 19 with a corresponding plurality of grabbing edges 32. Such an arrangement permits a surgeon to implant plural hair grafts at the same time. Other modifications can also be made to the above-described embodiments, which should therefore not be construed as limiting in any sense; rather, the invention should be measured only by reference to the appended claims.

What is claimed is:

1. An instrument for implanting a hair graft in a scalp incision comprising a one-way grabber and a sliding surface said one-way grabber being moveable relative to said sliding surface so as to sandwich the hairgraft therebetween, said one-way grabber being arranged to hold and then to drag a base end of the hair graft against at least part of said sliding surface toward the scalp incision and thence to a position at a bottom of the scalp incision, and to slide over the hair graft as the instrument is retracted from the scalp incision while leaving the hair graft in position in the scalp incision.

2. An instrument according to claim 1, wherein said sliding surface is comprised by an incision blade adapted to make the scalp incision.

3. An instrument according to claim 1, wherein said sliding surface is positionable at the bottom of the scalp incision and is withdrawn from the scalp incision before said one-way grabber is retracted therefrom.

4. An instrument for making a scalp incision and implanting a hair graft therein, comprising:

an elongate housing adapted to be manipulated by a surgeon during implantation of hair grafts, said elongate housing having a through bore for holding a supply of hair grafts and for feeding the hair grafts in a follicle-down orientation to a feed position;

a microsurgical blade arranged at the feed position of said elongate housing, said microsurgical blade having a longitudinally planar surface terminating in an incision tip, the longitudinally planar surface being adapted to guide a hair graft from the feed position to the incision tip; and a feed mechanism fixed to said elongate housing and adapted for manipulation by the surgeon between an unactuated position and a fully actuated position, said feed mechanism including a puller assembly terminating in a grabbing edge which, in the unactuated position, is positioned at the feed position adjacent the planar surface of said microsurgical blade, and which, in the fully actuated position, extends beyond the incision tip of said microsurgical blade;

wherein the grabbing edge is configured so that during manipulation from the unactuated position to the fully actuated position, the grabbing edge sandwiches the follicle end of a hair graft positioned at the feed position between the grabbing edge and the microsurgical blade, grabs the follicle end of the hair graft, slides the hair graft at least part way along the planar surface of said microsurgical blade, delivers the hair graft to the incision tip, and extends beyond the incision tip while the incision tip is withdrawn from the scalp incision, thereby to hold the hair graft in place at the base of the scalp incision.

5. An instrument according to claim 4, wherein said planar surface includes a groove extending from the feed position to the incision tip so as to guide the hair implant from the feed position to the incision tip.

6. An instrument according to claim 5, wherein said grabbing edge has a width wider than said groove so as to extend beyond the groove and cushion the hair graft.

7. An instrument according to claim 4, wherein plural microsurgical blades are arranged at the feed position and wherein said trigger actuated feed mechanism includes a corresponding plurality of grabbing edges.

8. An instrument according to claim 4, wherein the grabbing edge is chisel-shaped so as to provide for one-way grabbing of the follicle end of a hair graft while permitting sliding motion of the grabbing edge across the hair graft as the grabbing edge is withdrawn.

9. An instrument according to claim 4, wherein the grabbing edge is pointed so as to provide for one-way grabbing of the follicle end of a hair graft while permitting sliding motion of the grabbing edge across the hair graft as the grabbing edge is withdrawn.

10. An instrument according to claim 4, wherein the grabbing edge is toothed so as to provide for one-way grabbing of the follicle end of a hair graft while permitting sliding motion of the grabbing edge across the hair graft as the grabbing edge is withdrawn.

11. A method for micrograft implantation of hair grafts comprising the steps of:

making a scalp incision with a tip of a microsurgical blade;

providing a grabbing edge and a sliding surface, the grabbing edge being moveable relative to the sliding surface;

sandwiching a follicle end of a hair graft between the grabbing edge and the sliding surface;

grabbing the follicle end of the hair graft with the grabbing edge;

sliding the hair graft against at least a part of the sliding surface toward the scalp incision and thence to the base of the scalp incision using the grabbing edge;

holding the hair graft in place at the base of the scalp incision with the grabbing edge; and withdrawing the grabbing edge while leaving the hair graft implanted in the scalp incision.

12. A method according to claim 11, wherein said sliding step includes the step of guiding the hair graft down a groove in the surface of the microsurgical blade.

13. A method according to claim 11, wherein the sliding surface is comprised by the microsurgical blade, and wherein said sliding step slides the hair graft down at least a part of the microsurgical blade.

14. A method according to claim 13, wherein said sliding step leaves the tip of the microsurgical blade in the scalp incision, and wherein in said holding step the microsurgical blade is withdrawn from the scalp incision while the hair graft is held in place at the base of the scalp incision with the grabbing edge.

15. An instrument according to claim 2, wherein said incision blade is positionable at the bottom of the scalp incision and is withdrawn from the scalp incision before said one-way grabber is retracted therefrom.

\* \* \* \* \*